(12) United States Patent
Lee et al.

(10) Patent No.: US 12,383,226 B2
(45) Date of Patent: Aug. 12, 2025

(54) ULTRASONIC DIAGNOSTIC DEVICE HAVING LOCK MEMBER

(71) Applicant: ALPINION MEDICAL SYSTEMS CO., LTD., Hwaseong-si (KR)

(72) Inventors: Kang Jun Lee, Anyang-si (KR); Hyeon Jong Shin, Anyang-si (KR)

(73) Assignee: ALPINION MEDICAL SYSTEMS CO., LTD., Hwaseong-si (KR)

( * ) Notice: Subject to any disclaimer, the term of this patent is extended or adjusted under 35 U.S.C. 154(b) by 0 days.

(21) Appl. No.: 18/039,377

(22) PCT Filed: Nov. 9, 2021

(86) PCT No.: PCT/KR2021/016175
§ 371 (c)(1),
(2) Date: May 30, 2023

(87) PCT Pub. No.: WO2022/119159
PCT Pub. Date: Jun. 9, 2022

(65) Prior Publication Data
US 2024/0299008 A1    Sep. 12, 2024

(30) Foreign Application Priority Data

Dec. 4, 2020 (KR) .......................... 10-2020-0168243

(51) Int. Cl.
*A61B 8/00* (2006.01)
(52) U.S. Cl.
CPC ................ *A61B 8/44* (2013.01); *A61B 8/462* (2013.01)

(58) Field of Classification Search
CPC ........................................................ A61B 8/462
See application file for complete search history.

(56) References Cited

U.S. PATENT DOCUMENTS

| 4,625,731 | A  | * | 12/1986 | Quedens ................ A61B 8/462 |
|           |    |   |         |                         600/443 |
| 6,256,075 | B1 |   | 7/2001  | Yang |
| 6,430,038 | B1 |   | 8/2002  | Helot et al. |
| 6,669,639 | B1 |   | 12/2003 | Miller et al. |
| 7,448,583 | B2 |   | 11/2008 | Kim et al. |

(Continued)

FOREIGN PATENT DOCUMENTS

| JP | 2002-6990 A    | 1/2002 |
| JP | 2004-344636 A  | 12/2004 |

(Continued)

OTHER PUBLICATIONS

Korean Office Action issued on Jun. 19, 2023, in counterpart Korean Patent Application No. 10-2020-0168243 (3 pages in Korean).

*Primary Examiner* — Jason M Ip
(74) *Attorney, Agent, or Firm* — NSIP Law

(57) ABSTRACT

An ultrasonic diagnostic device having a lock member is disclosed. In the ultrasonic diagnostic device having a monitor support assembly for supporting a monitor for displaying ultrasound images according to an embodiment, the monitor support assembly comprises: a base mounted on a main body; a monitor arm rotatably provided on the upper side of the base; and a lock member which stops the rotation of the monitor arm when the monitor arm reaches a predetermined relative position with respect to the base.

3 Claims, 5 Drawing Sheets

(a)

(b)

(56) References Cited

U.S. PATENT DOCUMENTS

| | | | | |
|---|---|---|---|---|
| 2002/0011544 A1* | 1/2002 | Bosson | ................ | F16M 11/041 |
| | | | | 248/274.1 |
| 2002/0149906 A1* | 10/2002 | Ichimura | ............ | F16M 11/2014 |
| | | | | 361/679.06 |
| 2007/0023598 A1 | 2/2007 | Kim et al. | | |
| 2009/0294599 A1* | 12/2009 | Chen | .................... | G06F 1/1607 |
| | | | | 248/65 |
| 2012/0182709 A1 | 7/2012 | Asai et al. | | |
| 2014/0002962 A1* | 1/2014 | Mai | ....................... | G06F 1/1679 |
| | | | | 361/679.01 |
| 2016/0319986 A1* | 11/2016 | Hörndler | ................ | F16M 11/10 |

FOREIGN PATENT DOCUMENTS

| | | |
|---|---|---|
| JP | 5063313 B2 | 10/2012 |
| KR | 20-1986-0006528 U | 6/1986 |
| KR | 10-2000-0072847 A | 12/2000 |
| KR | 20-0234588 Y1 | 9/2001 |
| KR | 20-0267853 Y1 | 3/2002 |
| KR | 10-2004-0042299 A | 5/2004 |
| KR | 10-2007-0014536 A | 2/2007 |
| KR | 10-2009-0046230 A | 5/2009 |
| KR | 10-2012-0084267 A | 7/2012 |
| KR | 10-2012-0095213 A | 8/2012 |
| KR | 10-1673133 B1 | 11/2016 |

\* cited by examiner (a)          (b)

ULTRASONIC DIAGNOSTIC DEVICE HAVING LOCK MEMBER

CROSS REFERENCE TO RELATED APPLICATIONS

This application is a U.S. National Stage Application of International Application No. PCT/KR2021/016175, filed on Nov. 9, 2021, which claims the benefit under 35 USC 119(a) and 365(b) of Korean Patent Application No. 10-2020-0168243, filed on Dec. 4, 2020, in the Korean Intellectual Property Office, the entire disclosure of which is incorporated herein by reference for all purposes.

TECHNICAL FIELD

The present invention relates to ultrasound diagnostic technology, and more particularly, to an instrument structure of an ultrasonic diagnostic device.

The present invention was supported by the National Research and Development Project having grant number: 1425140041, project number: S2482471, department name: The Ministry of Small and Medium Enterprises and Start-ups, research management institution: Korea Institute for Advancement of Technology, research project name: WC300 R&D, research name: Development of Software Beamforming Ultrasound Diagnostic Apparatus Line Up, and research supervising institute: Alpinion Medical System Co., Ltd.

BACKGROUND ART

An ultrasonic diagnostic device has non-invasive and non-destructive characteristics and thus is widely used in various medical fields to obtain information on internal tissues of an object. In the ultrasonic diagnostic device, a probe emits an ultrasound signal to an object and receives an ultrasound echo signal reflected from the object. The main body of the ultrasonic diagnostic device performs signal processing on the ultrasound echo signal received from the probe to generate ultrasound data related to information on internal tissue of the object. In particular, ultrasonic diagnostic devices are used for medical purposes including observing an internal area of an object, detecting foreign substances, assessing injuries, imaging features, and the like.

DISCLOSURE

Technical Problem

According to an embodiment, an ultrasonic diagnostic device having a lock member capable of easily and quickly locking a monitor of the ultrasonic diagnostic device is proposed.

Technical Solution

In an ultrasonic diagnostic device having a monitor support assembly for supporting a monitor for displaying ultrasound images according to an embodiment, the monitor support assembly includes a base mounted on a main body, a monitor arm rotatably provided on the upper side of the base, and a lock member which stops the rotation of the monitor arm when the monitor arm reaches a predetermined relative position with respect to the base.

The lock member may include a lock pin, an elastic pressing member inserted into the lock pin, and a nut for compressing the elastic pressing member, and as the elastic pressing member is compressed when the nut is tightened, the elastic restoring force of the elastic pressing member may increase force for stopping the rotation of the arm.

By adjusting the degree of tightness of the nut of the lock member, the monitor arm may be fixed at a predetermined position without moving or rotating.

The elastic pressing member may be a compression spring.

The lock member may include a lock pin, a spring washer inserted into the lock pin, and a nut for compressing the spring washer, and as the spring washer is compressed when the nut is tightened, the elastic restoring force of the spring washer may increase force for stopping the rotation of the arm.

By adjusting the degree of tightness of the nut of the lock member, the monitor arm may be fixed at a predetermined position without moving or rotating.

The ultrasonic diagnostic device may further include a plurality of grooves formed on an edge of a rear surface of the monitor.

Advantageous Effects

According to an ultrasonic diagnostic device having a lock member in accordance with an embodiment, it is possible to easily and quickly lock a monitor of the ultrasonic diagnostic device. For example, the lock member locks upward and downward movement and left and right rotation of the monitor arm, and can lock the monitor without aligning the monitor to the center.

As the monitor is locked using the lock member, the monitor is fixed during transportation of the ultrasonic diagnostic device, which allows easy transportation. When the monitor is locked, it is easy to push and pull the monitor. Also, a user can easily lock the monitor.

When a nut is used in the lock member, it is possible to prevent inconvenient bolt fastening, which is problematic when using a bolt, and the bolt from being pulled out while transporting the ultrasonic diagnostic device.

MODES OF THE INVENTION

Figure 1:
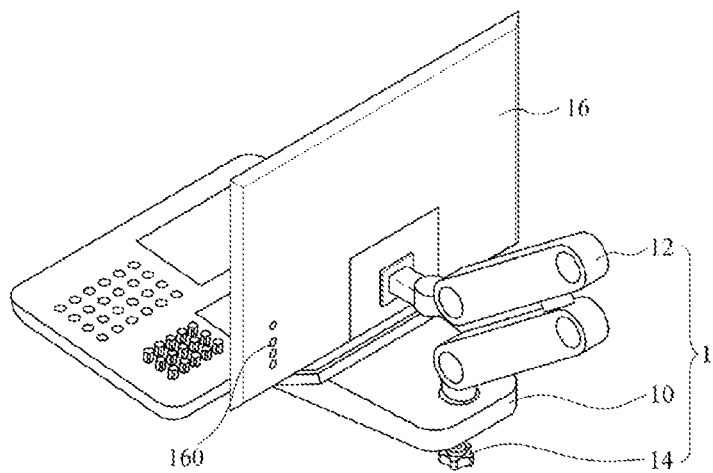
FIG. 1 is a diagram illustrating the configuration of an ultrasonic diagnostic device having a lock member according to an embodiment of the present invention.

The advantages and features of the present invention and the manner of achieving the advantages and features will become apparent with reference to embodiments described in detail below together with the accompanying drawings. However, the present invention may be implemented in many different forms and should not be construed as being limited to the embodiments set forth herein, and the embodiments are provided such that this disclosure will be thorough and complete and will fully convey the scope of the present invention to those skilled in the art, and the present invention is defined only by the scope of the appended claims. The same reference numerals refer to the same components throughout this disclosure.

In the following description of the embodiments of the present invention, if a detailed description of related known functions or configurations is determined to unnecessarily obscure the gist of the present invention, the detailed description thereof will be omitted herein. The terms described below are defined in consideration of the functions in the embodiments of the present invention, and these terms may be varied according to the intent or custom of a user or an operator. Therefore, the definitions of the terms used herein should follow contexts disclosed herein.

Hereinafter, embodiments of the present invention will be described in detail with reference to the accompanying drawings. However, the present invention may be realized in various forms, and the scope of the present invention is not limited to such embodiments. The embodiments of the present invention are provided to aid those skilled in the art in the explanation and the understanding of the present invention.

FIG. 1 is a diagram illustrating the configuration of an ultrasonic diagnostic device having a lock member according to an embodiment of the present invention. Referring to FIG. 1, an ultrasonic diagnostic device includes a monitor support assembly 1 and a monitor 16. The monitor 16 displays ultrasound images, and the monitor support assembly 1 supports the monitor 16.

The monitor support assembly 1 includes a base 10, a monitor arm 12, and a lock member 14. The base 10 is fixed to a main body (not shown) of the ultrasonic diagnostic device, and the monitor arm 12 is rotatably provided on the upper side of the base 10. For example, the monitor arm 12 may rotate left and right and move up and down.

The lock member 14 stops the rotation of the monitor arm 12 when the monitor arm 12 reaches a predetermined relative position with respect to the base 10. At this time, stopping the rotation is referred to as locking. For example, the lock member 14 locks the upward and downward movement and left and right rotation of the monitor arm 12. At this time, the locking member 14 is capable of locking the monitor 16 without aligning the monitor 16 to the center. As the monitor 16 is locked using the lock member 14, the monitor 16 is fixed during transportation of the ultrasonic diagnostic device, which allows easy transportation. When the monitor 16 is locked, it is easy to push and pull the monitor 16. Also, a user can easily lock the monitor 16. The structure of the lock member 14 will be described below with reference to FIGS. 3 to 5.

A plurality of grooves 160 are formed on the edge of the rear surface of the monitor 16 such that the user can conveniently move the monitor 16 by holding the grooves 160.

Figure 2:
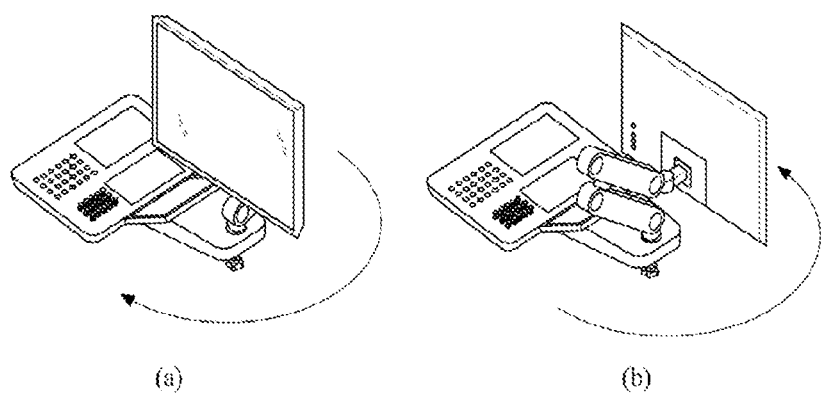
FIG. 2 is a diagram showing an example of locking a monitor while rotating the monitor left or right according to an embodiment of the present invention.

FIG. 2 is a diagram showing an example of locking a monitor while rotating the monitor left or right according to an embodiment of the present invention.

Referring to FIG. 2, according to an embodiment of the present invention, a lock member automatically stops the rotation of a monitor arm and fixes the monitor arm when the monitor arm reaches a predetermined relative position (e.g., 90 degrees to the left or 90 degrees to the right) when the monitor is rotated left or right. In this case, it is possible to lock the monitor without aligning the monitor to the center. The same principle applies when the monitor is moved up or down. After the monitor is locked, the user may release the locking by manually rotating the monitor left and right with a force greater than the static friction force.

Figure 3:
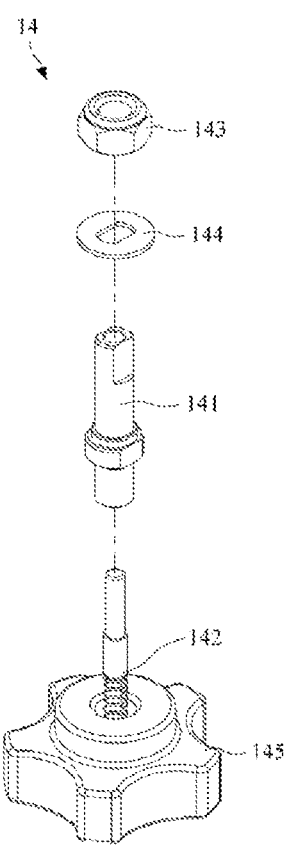
FIG. 3 is a view of a disassembled lock member according to an embodiment of the present invention.
Figure 4:
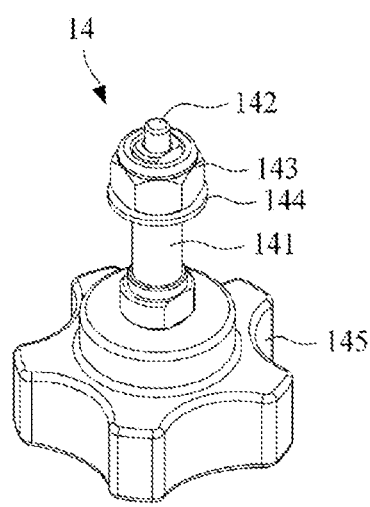
FIG. 4 is a view of the assembled lock member of FIG. 3.

FIG. 3 is a view of a disassembled lock member according to an embodiment of the present invention, and FIG. 4 is a view of the assembled lock member of FIG. 3.

Referring to FIGS. 3 and 4, a lock member 14 includes a lock pin 141, an elastic pressing member 142, a nut 143, a flat washer 144, and a handle 145.

The elastic pressing member 142 is inserted into the lock pin 141, and the nut 143 compresses the elastic pressing member 142 when tightened and releases the elastic pressing member 142 when loosened. As the elastic pressing member 142 is compressed, the elastic restoring force of the elastic pressing member 142 increases the force for stopping the rotation of the monitor arm. The elastic pressing member 142 may be a compression spring.

As the nut 143 is more tightened, the degree of compression deformation of the elastic pressing member 172 increases, and correspondingly the degree to which the monitor arm is pressed toward the base increases (i.e., the force for stopping the rotation of the monitor arm increases). Accordingly, the static friction force between the monitor arm and the flat washer 144 increases, which hinders the rotation of the monitor arm. Since the friction force between the flat washer 144 and the monitor arm 12 changes according to the degree of tightness of the nut 143, the monitor arm 12 may be fixed at a specific position without rotating by adjusting the degree of tightness of the nut 143.

The static friction force for stopping the monitor is set according to the magnitude of the elastic restoring force of the elastic pressing member 142, which is changed by tightening or loosening the nut 143, and it will be understood that the setting may vary according to various monitors that can be used in the ultrasonic diagnostic device.

When the nut 143 is used, it is possible to prevent inconvenient bolt fastening, which is problematic when using a bolt, and the bolt from being pulled out while transporting the ultrasonic diagnostic device.

In a situation where the rotation of the monitor arm is stopped by the static friction force caused by the elastic restoring force of the elastic pressing member 142, when the user applies force to the monitor to move it to a desired position, the torque associated with the rotation of the monitor arm is increased. When the increased torque becomes greater than the static friction force, the monitor arm can rotate, so that the user can move the monitor to the desired position.

Figure 5:
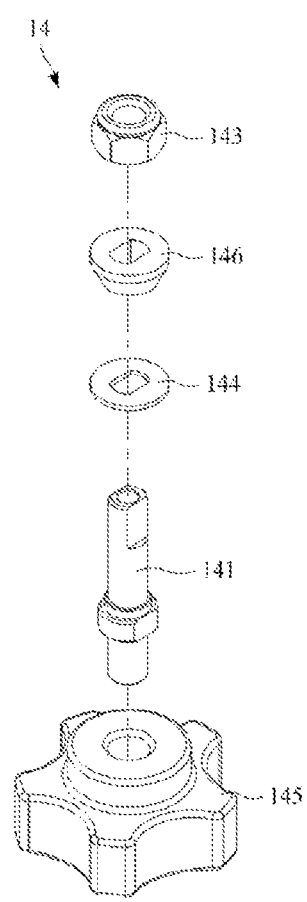
FIG. 5 is a view of a disassembled lock member according to another embodiment of the present invention.

FIG. 5 is a view of a disassembled lock member according to another embodiment of the present invention.

Referring to FIG. 5, unlike the example shown in FIG. 3, a spring washer 146 is used instead of the elastic pressing member 142, and the principle thereof is similar to the elastic spring washer 146. The spring washer 146 is inserted into a lock pin, and a nut 143 compresses the spring washer 146 when tightened and releases the spring washer 146 when loosened. The elastic restoring force of the spring washer 146 increases force for stopping the rotation of a monitor arm to stop the monitor. The monitor arm may be fixed at a predetermined position without moving or rotating by adjusting the degree of tightness of the nut 143.

Heretofore, the present invention has been described by focusing on the exemplary embodiments. It can be understood by those skilled in the art to which the present invention pertains that the present invention can be implemented in modified forms without departing from the essential feature of the present invention. Therefore, the disclosed embodiments should be considered as illustrative rather than determinative. The scope of the present invention is defined by the appended claims rather than by the foregoing description, and all differences within the scope of equivalents thereof should be construed as being included in the present invention.

The invention claimed is:

1. An ultrasonic diagnostic device having a monitor support assembly for supporting a monitor for displaying ultrasound,
    wherein the monitor support assembly comprises:
    a base mounted on a main body;
    a monitor arm rotatably provided on an upper side of the base to allow left and right rotation around the vertical axis; and
    a lock member located at a lower part of the base which stops left and right rotation of the monitor arm when the monitor arm reaches a predetermined relative position with respect to the base during left and right rotation of the monitor around the vertical axis,
    wherein the lock member comprises:
    a lock pin;
    an elastic pressing member or a spring washer inserted into the lock pin;
    a nut for compressing the elastic pressing member or the spring washer; and
    a handle configured to be rotated to adjust the degree of tightness of the nut, wherein tightening the nut increases a force for stopping the rotation of the monitor arm, and further tightening allows the monitor arm to be fixed at a specific position without moving or rotating, and the monitor arm remains fixed unless a user applies force greater than a static friction force.

2. The ultrasonic diagnostic device of claim 1, wherein the elastic pressing member is a compression spring.

3. The ultrasonic diagnostic device of claim 1, further comprising a plurality of grooves formed on an edge of a rear surface of the monitor.

* * * * *